United States Patent [19]

Ward et al.

[11] Patent Number: 4,941,882
[45] Date of Patent: Jul. 17, 1990

[54] ADHESIVE DRESSING FOR RETAINING A CANNULA ON THE SKIN

[75] Inventors: William J. Ward; Joanne Shorthouse, both of Hull, United Kingdom

[73] Assignee: Smith and Nephew Associated Companies, p.l.c., United Kingdom

[21] Appl. No.: 165,627

[22] Filed: Mar. 8, 1988

[30] Foreign Application Priority Data

Mar. 14, 1987 [GB] United Kingdom ............... 8706116

[51] Int. Cl.$^5$ ............................................. A61M 5/32
[52] U.S. Cl. ............................ 604/180; 128/DIG. 26; 604/305
[58] Field of Search .......... 128/155, DIG. 26, 207.17, 128/335; 604/180, 239, 240, 289, 305

[56] References Cited

U.S. PATENT DOCUMENTS

| | | |
|---|---|---|
| 4,275,721 | 6/1981 | Olson . |
| 4,310,509 | 1/1982 | Berglund et al. ............... 128/156 X |
| 4,541,426 | 9/1985 | Webster ............................ 128/156 |
| 4,598,004 | 7/1986 | Heinecke ........................ 128/156 X |
| 4,685,455 | 8/1987 | Vrouenraets ...................... 128/156 |

FOREIGN PATENT DOCUMENTS 2035096 6/1980 United Kingdom ............... 604/180

*Primary Examiner*—Randall L. Green
*Assistant Examiner*—Paul Prebilic
*Attorney, Agent, or Firm*—Jacobs & Jacobs

[57] ABSTRACT

A dressing for retaining a cannula on the skin is described. The dressing comprises a backing film coated on one face with an adhesive layer and with first and second release sheets covering the adhesive layer. A hole and a dividing line are cut through the dressing and second release sheet so that the dividing line extends from the hole to one edge of the dressing and the edge of the second release sheet. In use when the second release sheet is removed the hole in the dressing fits around the indwelling cannula. In a preferred form a portion of the dressing comprises an adhesive coated handle which is stiffer than the remainder of the dressing and which carries the hole and dividing line.

12 Claims, 1 Drawing Sheet

ADHESIVE DRESSING FOR RETAINING A CANNULA ON THE SKIN

The present invention relates to an adhesive dressing which is suitable for use on skin for the fixation of a catheter or a cannula and which comprises a backing film coated on one face with an adhesive layer and first and second release sheets covering the adhesive layer and which dressing is adapted to adhere around a connection device at the proximal end of the cannula or catheter to prevent ingress of bacteria to the injection site; to methods of their preparation and use.

Adhesive dressings such as OpSite (Trademark) are frequently used to cover and secure a catheter or cannula in place at an intravenous access site. Such dressings may be referred to as i.v. dressings.

Commercially available i.v. dressings typically comprise a thin moisture vapour permeable sheet material which has on one surface a skin compatible pressure sensitive adhesive which is in turn covered by a single sheet removable protector. In use the dressing is adhered so as to cover the intravenous access site and the catheter or cannula. One problem with such dressings is that usually a bulky connector or hub is present at the proximal end of the catheter or cannula whereby connection can be made with a source of infusion fluid. This is usually in the form of a female luer lock component. Other devices may be present at this hub such as taps or injection ports or the like. The connector or hub being necessarily exposed to the atmosphere can provide a pathway whereby bacteria may reach the injection site since the connector cannot be totally enclosed beneath the dressing. One way of overcoming this problem is to use two types of dressing one covering the injection site and the second ensuring that bacteria cannot migrate from the connector along the catheter or cannula to the injection site.

A dressing has now been developed which simplifies the protection of injection sites for indwelling catheters and cannulae by providing a dressing which both covers the injection site and is adapted to retain any connector associated with the catheter or cannula in place with reduced risk of bacteria migrating to the injection site.

A second problem which is sometimes observed with such dressings is that once the protector has been removed the thin filmic adhesive dressing creases, puckers or otherwise sticks to itself and must be discarded. Many dressings have therefore included extra stiffening layers or frames or handles in an attempt to overcome this problem. However, the dressings of this invention mitigate this problem by providing the protector as a first release sheet and a second release sheet so that the first release sheet is removed to expose the adhesive on the part of the dressing which is to cover the injection site and the second release sheet is then removed to expose the remaining adhesive surface which is used to maintain the catheter or cannula in place. The second release sheet, which is folded, stabilises the dressing after removal of the first sheet and during application of the dressing.

Accordingly the present invention provides a dressing for retaining a cannula comprising a backing film coated on one face with an adhesive layer and first and second release sheets covering the adhesive layer characterised in that there is a hole and a dividing line through the dressing and second release sheet said dividing line extending from the hole to one edge of the dressing and second release sheet whereby when the second release sheet is removed the hole in the dressing is adapted to be placed around the cannula.

By dividing line is meant a means to enable the dressing on one side of the dividing line to be separated from the dressing on the other side. A dividing line may include for example cuts and lines of perforations. Preferably the dividing line is a line of perforations.

The dividing line allows the hole and the part of the dressing around the dividing line to be placed easily around, and subsequently secure, a catheter or cannula lying on the skin.

Suitable backing films include polymeric films, papers, woven and nonwoven fabrics, but preferably the backing film comprises a flexible polymeric film. The film may comprise any of the flexible polymeric films conventionally used in i.v. dressings. The flexible film is aptly a moisture vapour permeable and bacteria proof film. In addition it is most convenient to employ a transparent material. Favoured moisture vapour permeable, liquid water impermeable, flexible films will have a moisture vapour transmission rate of at least 300 $gm^{-2}$ 24 $h^{-1}$ at 37° C. at a relative humidity difference of 100% to 10%, more suitably at least 400 $gm^{-2}$ 24 $h^{-1}$, preferably at least 500 $gm^{-2}$ 24 $h^{-1}$ and most preferably at least 700 $gm^{-2}$ 24 $hr^{-1}$.

Suitable flexible films for use in the invention include those described in British Patent No. 1280631 and European Patent Application Nos. 51935, 178740 and 196459. Favoured flexible polymeric films include those formed from a polyether or polyester polyurethane. Suitable polyether and polyester polyurethanes include those known as Estanes (Trademark, available from B. F. Goodrich Corp.). Preferred polyurethanes are available as Estanes 5701, 5702, 5703, 5714 and 580201. A second particularly favoured flexible film may be formed from an elastomeric polyether polyester. Preferred polyether polyesters include Hytrel 4056 (Trademark, available from E. I. du Pont de Nemours & Co.). A third particularly favoured polymeric flexible film may be formed from a polyether polyamide. Preferred polyether polyamides include Pebax 4011 (Trademark).

Suitably the thickness of the flexible films used in the invention may be from 9 to 80μm, more suitably 15 to 50μm and preferably 20 to 40μm for example 25μm, 30μm or 35μm.

A second favoured form of flexible film may be formed from any moisture vapour permeable transparent hydrophilic polymer. Suitable materials include polyurethanes, polyether polyesters, polyether polyamides, cellulosics and the like.

A favoured flexible film of hydrophilic polymer is formed from a hydrophilic polyurethane. Suitable hydrophilic polyurethanes include those having the composition and prepared by the process described in British Patent No. 2093190B. Favoured hydrophilic polyurethanes are those which contain from 5 to 50% by weight of water when hydrated, more suitably 10 to 40% by weight of water and which have a thickness when present in a dressing of from 15 to 80μm, more suitably 20 to 45μm. A preferred film of hydrophilic polyurethane has a water content when hydrated of 20 to 30% for example 25% and a thickness of 20 to 45μm, for example 30μm.

Suitably the adhesive layer on the dressing may be 15 to 65μm thick, preferably is 20 to 40μm thick, for example 25, 30 or 35μm thick. Such adhesive layers will generally have a weight of adhesive per unit area of 10 to 75 gm$^{-2}$, more usually 15 to 65 gm$^{-2}$ and preferably 26 to 40 gm$^{-2}$.

Suitable adhesives include those which are described in British Patent No. 1280631 and European Patent Applications Nos. 51935, 35399. Preferably, the adhesive is a polyvinyl ether adhesive such as polyvinyl ethyl ether adhesive or an acrylate adhesive such as an acrylate ester copolymer adhesive. Examples of the latter include acrylate ester copolymers which contain hydrophilic groups, for example a copolymer of 47 parts by weight butyl acrylate, 47 parts by weight 2-ethylhexyl acrylate and 6 parts by weight acrylic acid.

The adhesive may be applied to the backing film as a continuous layer or as a discontinuous layer for example as a pattern spread layer, a porous layer.

Since the dressings of the present invention are to be adhered to normal healthy skin then to avoid maceration of that skin it is arranged that the dressing will have a moisture vapour permeability of at least 300 gm$^{-2}$ 24 h$^{-1}$ at 37° C. and 100% to 10% relative humidity, more suitably will be at least 500 gm$^{-2}$ 24 h$^{-1}$ and preferably will be at least 700 gm$^{-2}$ 24 h$^{-1}$.

Suitably the adhesive may contain a medicament such as an antibacterial agent. Suitably the adhesive may contain from 1 to 10% by weight of the adhesive as medicament.

Suitable antibacterial agents include chlorhexidine and salts thereof such as chlorhexidine diacetate and chlorhexidine digluconate, iodophors such as polyvinyl pyrrolidone-iodine, silver salts such as silver sulphadiazine and polymeric biguanides for example those antibacterial agents known as Vantocil (Trademark) which is polyhexamethylene biguanide hydrochloride.

In a preferred dressing the adhesive contains 5% by weight of the adhesive of chlorhexidine diacetate.

In a preferred form of this dressing one portion of the dressing is a handle. The handle will have an adhesive layer on one surface so that it may be adhered to the skin of the patient when the dressing is in place. Normally prior to application of the dressing this adhesive layer will be covered by the second release sheet. In use the handle and its associated release sheet may be held in the hand whilst the first release sheet is removed from the remainder of the dressing. The adhesive coated layer is then applied over the skin puncture site. The second release sheet may then be removed and the handle adhered to the skin. The handle is made from a different material to the rest of the dressing and since it is not meant to cover the skin puncture site need not be bacterial-proof through this property is desirable. It is clear therefore that in a preferred form the backing layer of the dressing comprises a handle and a flexible sheet which forms the rest of the dressing. The flexible sheet is aptly formed from any of the materials which are suitable for the backing layer as described hereinbefore especially a moisture vapour permeable, liquid water impermeable, flexible polymeric film. The handle may be attached to the rest of the dressing by any conventional means such as adhesives or by bonding the handle and flexible sheet together by means of heat. In this preferred form of the dressing the hole and dividing line are located in the handle of the dressing.

From the foregoing it is clear that the adhesive surface on the handle and the adhesive surface on the flexible sheet will be on the same side so that both may be adhered to the body.

The handle used in the dressing of the invention can suitably be a film, sheet or web. Suitable handles can be made of a wide variety of materials including paper, non-woven fabric, woven fabric and films, sheets or webs of polymers including polypropylene, polyethylene, copolymers thereof and blends thereof and blends including polystyrene, polyester and polyvinyl chloride.

Particularly apt materials for forming the handle include paper, porous polyvinyl chloride sheet such as that sometimes known as Porvic (Trademark) which is conventionally used in the manufacture of first aid dressings, non-woven fabric such as spun-bonded polyester fabric (Sontara, Trademark), polyester film (Melinex, Trademark), woven acrylic fabric, embossed films of low or high density polyethylene or polypropylene, integral nets formed by the fibrillation of embossed films and oriented polypropylene films.

However, particularly preferred materials for forming the handle are integral nets particularly those formed by the fibrillation of thermoplastic embossed polyolefin films comprising low and high density polyethylene, polypropylene or copolymers or blends thereof or blends of polyolefin with polystyrene. Such nets are described in British Patents Nos. 1495151 and 1531715.

The handle has a dividing line extending inwardly from the edge of the handle in a direction towards the flexible sheet portion of the backing film of the dressing. The dividing line leads to the hole cut within the area of the handle. The hole preferably extends into the overlap area where the handle and flexible sheet overlap.

The hole may be of any shape such as square, rectangular, circular, oval and the like. It is preferred that the hole is oval in shape as this shape accommodates the shape of the connector and thereby forms a better seal between the dressing and the connector. Suitably the long axis of the hole may be from 20 to 30 mm in length and preferably 23 to 27 mm in length for example 25 mm and the short axis of the hole may be from 5 to 15 mm, and preferably 7 to 11 mm for example 9 mm.

The second release sheet which may cover the exposed adhesive of the handle when present may be in a folded form and may be cut along with the handle so that the release sheet has a slit and opening or alternatively the release sheet may be merely perforated.

The handle may be colour coded, for example the handle may be green or yellow or pink.

Since the handle is to be adhered to the skin it is preferred that the handle when coated with adhesive should have a moisture vapour transmission rate of at least 300 gm$^{-2}$ 24 h$^{-1}$ at 37° C. and 100% to 10% relative humidity when measured by the Payne Cup Method. More suitably the adhesive coated handles should have a rate of at least 500 gm$^{-2}$ 24 h$^{-1}$ and preferably should be at least 700 gm$^{-2}$ 24 h$^{-1}$. The handle may then be safely adhered to the skin without the risk of causing maceration to the underlying normal healthy skin.

An adhesive such as one of those described in British Patent No. 1280631 or European Patent Application No. 35399 may be spread onto the smooth surface of the net as hereinbefore described, that is the one which was embossed with the series of grooves. A particularly suitable adhesive is an acrylate ester copolymer adhesive formed from the polymerisation of 47 parts 2-ethylhexyl acrylate, 47 parts butyl acrylate and 6 parts acrylic acid. This combination of net and adhesive gives a tape of both high moisture vapour permeability which is particularly apt for the dressings of the present invention. If the adhesive layer is continuous the moisture vapour transmission rate is approximately 800 gm$^{-2}$ 24 h$^{-1}$ and if the adhesive layer is porous the rate may be as high as 8000 gm$^{-2}$ 24 h$^{-1}$, when measured at 37° C. and 100% to 10% relative humidity.

Suitably the handle may be 1.0 cm to 6.0 cm in width and preferably 2.0 to 5.0 cm in width, for example 2.8 cm, 3.0 cm or 3.8 cm in width. The width of the margin of the handle which is adhered to the edge margin of the flexible sheet is then suitably 0.1 to 1.0 cm, more suitably is 0.15 to 0.5 cm and is preferably 0.2 to 0.3 cm.

In order to avoid maceration of the underlying skin in this overlap area of the flexible sheet and handle the dressing in this area will favourably have a moisture vapour transmission rate of at least 300 g$^{-2}$ 24 h$^{-1}$ at 37° C. and 100% to 10% relative humidity difference, more favourably the rate will be at least 500 gm$^{-2}$ 24 h$^{-1}$ and preferably be at least 700 gm$^{31\ 2}$ 24 h$^{-1}$.

In a further embodiment of this invention a further handle may be placed on the edge of the dressing opposite the handle with the dividing line and hole.

Suitable release sheets for covering exposed adhesive areas prior to use include silicone release coated papers and plastics coated papers and release coated films such as silicone coated polyethylene. A favoured release sheet is a silicone release/polyethylene coated paper known as Steralease No. 15 (Trademark, available from Sterling Coated Paper Limited).

The adhesive layer of the dressing is protected by a first and second release sheet.

In a preferred form the second release sheet protects the adhesive layer on the handle and is folded back to form a second tab. The first release protects the adhesive layer on the flexible sheet of the dressing and a part of this first release sheet, which is not in contact with the adhesive layer, forms a first tab which covers part of the second tab. Preferably the second tab is longer than the first tab. In a further preferred embodiment the second tab when folded back extends beyond the edge of the dressing.

Preferably the second release sheet which protects the adhesive layer on the handle has a hole and a dividing line in it matching exactly the hole and dividing line in the handle.

In a further preferred form of the dressing a portion is cut out of the second tab so that when it is folded back on the second release sheet the cut-out portion of the second tab will overlay that portion of the hole in the second release sheet covered by the second tab. Preferably the first tab has an aperture cut so that when it covers the second tab the edges of the aperture line up with the edges of the hole in the second release sheet and the handle.

The dressing of the invention will usually have a rectangular shape. Suitable dressings have a size of 5 cm×5 cm to 20 cm×20 cm for example 6 cm×8 cm, 10 cm×10 cm, 10 cm×15 cm, 15 cm×15 cm etc.

The dressing of the invention is preferably sterile. The dressing of the invention is advantageously provided within a bacteria proof pack such as a sealed aluminium foil or paper/plastics film pouch. Sterilization of the dressing can be carried out by a conventional sterilizing method such as ethylene oxide, electron or gamma radiation.

In another aspect the invention provides a process of making a dressing of the invention which comprises attaching the edge margin of a handle to an edge margin of a flexible sheet and then the handle has a dividing line cut inwardly from one side edge and a hole punched in the handle area.

Suitable backing films, flexible sheets and handles for use in the process of the invention are described hereinbefore in relation to the dressing of the invention.

The backing film may be formed by casting or extrusion onto a support film, usually the non-release surface of a conventional release paper or polymer. The adhesive layer may be formed by casting or transfer coating onto the surface of the flexible film. The adhesive surface of the flexible film may then be transferred onto the release surface of the second release sheet and then the first release sheet placed over the remaining adhesive surface so that the tab portion overlaps onto the second release sheet. The three layer laminate is then cut into a strip having the width of the required dressing. The dividing line and hole are then cut in the dressing.

The handle when present may be formed by transfer coating an adhesive layer on a release paper onto the material forming the handle. This may then be cut into a strip of the appropriate width and attached to the edge of the flexible sheet portion of the backing film. The second release sheet is applied to the adhesive surface of the handle and the first release sheet is applied to the adhesive surface of the flexible sheet. The dividing line and hole are then cut in the handle area and second release sheet.

In another aspect the present invention provides a method for retaining a cannula on the body employing a dressing comprising a backing film coated on one face with an adhesive layer and first and second release sheets covering the adhesive layer in which there is a hole and a dividing line through the dressing said dividing line extending from the hole to one edge of the dressing and second release sheet which method comprises separating the dressing along the dividing line and placing the part of the dressing containing the hole around the cannula, removing the first release sheet and adhering the exposed part of the dressing over the puncture site and then removing in turn the two halves of the second release sheet so that the remainder of the dressing secures the cannula on the skin.

A preferred embodiment of the present invention will now be described with reference to the accompanying drawings in which.

Figure 1:
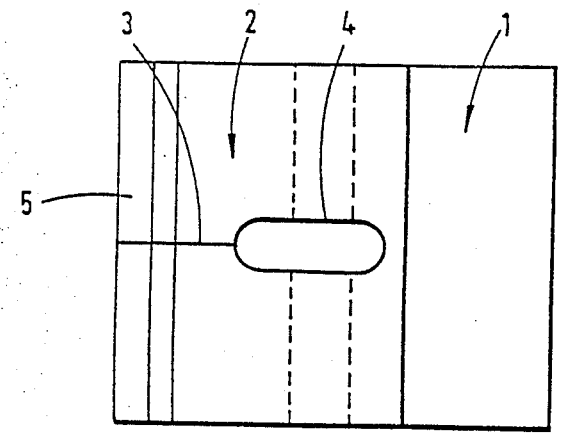
FIG. 1 shows a plan view of a dressing of the invention.

FIG. 1 shows a view from above of a dressing of the present invention. The adhesive coated flexible sheet portion of the backing film (1) is adhered to the skin over the injection site. An adhesive coated handle (2) is attached along one edge to the adhesive coated flexible sheet (1). The handle (2) has extending inwardly from one side edge a dividing line (3) and at the end of the dividing line (3) but within the boundaries of the handle (2) is a hole (4). The exposed adhesive surfaces of the flexible sheet (1) and the handle (2) are covered by first and second release sheets respectively which are removed prior to use. The second release sheet (5) which covers the adhesive on the handle (2) is in the form of a folded piece of silicone release paper which may carry a dividing line and hole similar to that of the handle (2) or may be perforated along the line of the dividing line (3) in the handle.

Figure 2:
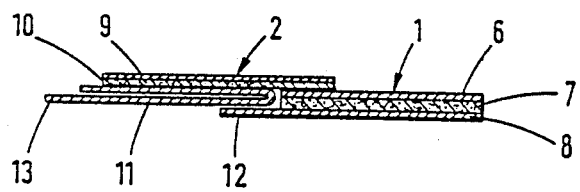
FIG. 2 shows a cross-section through a dressing of the invention illustrating the layers which are present therein.

FIG. 2 shows a cross-section through a dressing of the invention showing the different layers which make up the dressing. The adhesive coated flexible sheet (1) comprises two layers, first a backing film (6) which is formed from a moisture vapour permeable polymeric film comprising for example a linear polyether or polyester polyurethane, an elastomeric polyester or other hydrophilic polymer film which has a moisture vapour transmission rate of over 1600 gm$^{-2}$ 24 h$^{-1}$ at 37° C. and 100% to 10% relative humidity difference. Second an adhesive layer (7) which is formed from a skin compatible adhesive such as a polyvinylethyl ether or polyacrylate ester copolymer adhesive. Suitably the adhesive is moisture vapour permeable whereby the dressing has a moisture vapour transmission rate of over 300 gm$^{-2}$ 24 h$^{-1}$. Prior to use the adhesive surface is covered by a first release sheet (8) formed from a silicone coated release paper. The handle (2) is also formed from 2 layers (9,10). The first a backing layer (9) is more rigid than the backing film (1) but is also formed from a moisture vapour permeable material. Since this material is adhered to unbroken skin, the backing layer (9) may be a plasticised polyvinyl chloride film, a non-woven fabric or a net. The second layer (10) is an adhesive layer similar to that on the flexible sheet (1). The handle (2) is adhered to the adhesive coated flexible sheet (1) along one edge and the remaining exposed adhesive surface is covered by a silicone-coated second release sheet (11) suitably in the form of a folded piece. The first release sheet (8) overlaps part of the second release sheet (11) to ensure that no adhesive surfaces are left exposed. The first (12) and second (13) tabs on the first and second release sheets respectively allow the release sheets to be removed easily.

Figure 3:
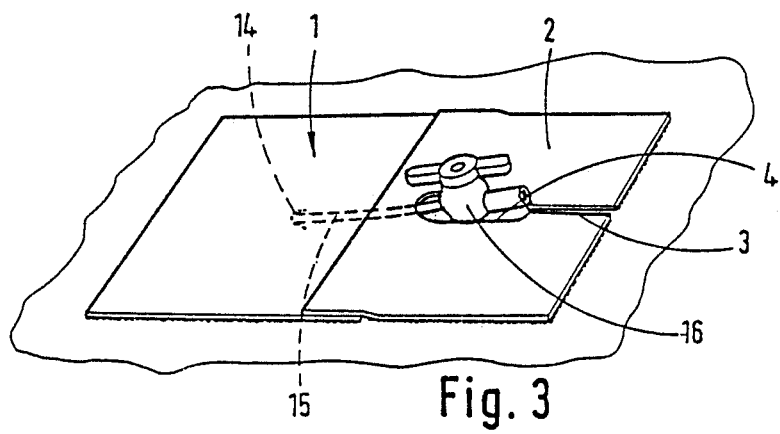
FIG. 3 shows a dressing of the invention adhered to the skin and around a tap connector.

FIG. 3 shows a dressing of the invention in position at an injection site. The adhesive coated flexible sheet (1) is adhered over the injection site (14) and over the indwelling catheter (15). The hole (4) and the dividing line (3) in the handle (2) are adapted to fit round a connector (16) which in this illustration carries a tap.

In use the second tab (13) and handle (2) are held in one hand and the first tab (12) is held in the other hand. The first tab (12) is then pulled and the first release sheet (8) is removed from the adhesive coated flexible sheet (1). The adhesive coated backing film (1) is then adhered over the injection site and the catheter or cannula. The second tab (13) is then grasped and pulled and the second release sheet (11) is removed. The dividing line (3) in the dressing enables the dressing to be placed around the connector (16) so that the hole (4) in the dressing goes around the connector (16) and the two parts of the handle (2) can be adhered to the skin around the connector (14).

Alternatively the dressing may be used as follows, the perforated dividing line (3) is torn through and the two arms of the handle (2) and the hole (4) are arranged to lie on either side of the connector (16). The first tab (12) is used to remove the release sheet (8) from the adhesive surface of the flexible sheet (1) and this portion of the dressing is adhered to the skin over the injection site (14) and the indwelling catheter (15). The second tab (13) now in two parts is used to expose in turn the adhesive surfaces of the handle (2) surrounding the connector (16) which are then adhered to the skin around the connector. Alternatively each half of the second tab in turn can be used to expose the adhesive surfaces of the divided handle such that the handle halves cross one on top of the other on the skin under the connector to form a better seal around the connector and to secure the connector more firmly.

We claim:

1. A dressing for retaining cannulae comprising a backing film coated on one surface with an adhesive layer, the backing film comprising an adhesive coated flexible sheet attached to an adhesive coated handle, the material of the handle being different from the material of the flexible sheet, first and second release sheets covering the adhesive layer in which there is a hole and a dividing line through the dressing and the second release sheet said dividing line extending from the hole to one edge of the dressing and the second release sheet, the second release sheet contacting the adhesive surface of the handle and the hole and dividing line being located within the handle, whereby when the second release sheet is removed the hole in the dressing is adapted to be placed around a cannula.

2. A dressing according to claim 1 in which the dividing line is a line of perforations.

3. A dressing according to claim 1 in which the hole is oval in which the long axis is from 20 to 30 mm and the short axis is from 5 to 15 mm.

4. A dressing according to claim 1 in which part of said second release sheet is folded back to form a second tab and a part of said first release sheet which is not in contact with the adhesive layer forming a first tab which covers part of said second tab, and wherein the second tab extends beyond the first tab.

5. A dressing according to claim 1 in which the flexible sheet is a polyurethane film of thickness from 15 to 50 μm and the handle is an integral net formed by the fibrillation of thermoplastic embossed polyolefin film.

6. A dressing according to claim 1 in which the backing film is a polyurethane film of thickness from 15 to 50 μm.

7. A dressing according to claim 1 in which the adhesive layer is formed from a acrylate ester copolymer adhesive and which has a weight per unit area of 10 to 75 gm$^{-2}$.

8. A dressing according to claim 1 in which the backing film coated with an adhesive layer has a moisture vapour transmission rate of at least 300 gm$^{-2}$24 h$^{-1}$ at 37° C. and 100% to 10% relative humidity difference.

9. A dressing according to claim 1 in which the adhesive layer contains antibacterial agent.

10. A dressing according to claim 9 in which the adhesive layer contains 5% by weight of the adhesive layer as the antibacterial agent chlorhexidine diacetate.

11. A dressing according to claim 1 in which the dressing is sterile and is provided in a bacteria proof pack.

12. A dressing according to claim 5 in which the adhesive coated handle has a continuous adhesive layer and has a moisture vapour transmission rate of at least 800 gm$^{-2}$24 H$^{-1}$ at 37° C. and 100% to 10% relative humidity difference.

* * * * *